United States Patent
Tjäder et al.

(10) Patent No.: US 11,628,088 B2
(45) Date of Patent: Apr. 18, 2023

(54) ULTRASONICALLY DETECTABLE INTRAUTERINE SYSTEM AND A METHOD FOR ENHANCING ULTRASOUND DETECTION

(71) Applicant: BAYER OY, Turku (FI)

(72) Inventors: Taina Tjäder, Littoinen (FI); Sara Heinonen, Tampere (FI)

(73) Assignee: Bayer OY, Turku (FI)

( * ) Notice: Subject to any disclaimer, the term of this patent is extended or adjusted under 35 U.S.C. 154(b) by 309 days.

(21) Appl. No.: 14/569,616

(22) Filed: Dec. 12, 2014

(65) Prior Publication Data

US 2015/0164684 A1    Jun. 18, 2015

Related U.S. Application Data

(63) Continuation of application No. 11/887,901, filed as application No. PCT/FI2006/050123 on Apr. 4, 2006, now abandoned.

(30) Foreign Application Priority Data

Apr. 5, 2005    (FI) .................................. 200550345

(51) Int. Cl.
| | |
|---|---|
| *A61F 6/06* | (2006.01) |
| *A61F 6/14* | (2006.01) |
| *A61B 8/08* | (2006.01) |
| *A61M 31/00* | (2006.01) |

(52) U.S. Cl.
CPC ............ *A61F 6/144* (2013.01); *A61B 8/0841* (2013.01); *A61B 8/481* (2013.01); *A61M 31/002* (2013.01)

(58) Field of Classification Search
CPC ............ A61F 6/144; A61F 6/142; A61F 6/14; A61F 6/00; A61F 6/06; A61K 9/0039; A61K 9/0036
See application file for complete search history.

(56) References Cited

U.S. PATENT DOCUMENTS

| | | |
|---|---|---|
| 3,230,953 A | 1/1966 | Birnberg |
| 3,515,132 A | 6/1970 | McKnight |
| 3,633,574 A | 1/1972 | Lerner |
| 3,777,748 A | 12/1973 | Abramson |
| 3,811,435 A | 5/1974 | Soichet |

(Continued)

FOREIGN PATENT DOCUMENTS

| | | |
|---|---|---|
| CA | 1178864 A | 12/1984 |
| DE | 2207939 | 8/1973 |

(Continued)

OTHER PUBLICATIONS

English Language Translation of EP0147274 A1.

(Continued)

*Primary Examiner* — Victoria J Hicks
(74) *Attorney, Agent, or Firm* — McBee, Moore & Vanik IP, LLC

(57) ABSTRACT

The present invention relates to ultrasonically detectable intrauterine systems and to a method for enhancing ultrasound detection of these systems. An intrauterine system having an inert metal coating on at least part of the body of the intrauterine system or at least one inert metal clip, pin, ring or sleeve fixedly positioned on the body of the intrauterine system is described.

17 Claims, 8 Drawing Sheets

(56) References Cited

U.S. PATENT DOCUMENTS

| | | | |
|---|---|---|---|
| 3,913,573 A | 10/1975 | Gutnick | |
| 3,935,860 A | 2/1976 | Hoff | |
| 3,973,560 A * | 8/1976 | Emmett | A61F 6/142 128/833 |
| 4,034,749 A | 7/1977 | Von Kesseru et al. | |
| 4,658,810 A * | 4/1987 | Bauer | A61F 6/142 128/839 |
| 4,807,610 A * | 2/1989 | Gainutdinova | A61F 6/144 128/830 |
| 4,869,259 A | 9/1989 | Elkins | |
| 4,977,897 A | 12/1990 | Hurwitz | |
| 5,201,314 A | 4/1993 | Bosley et al. | |
| 5,289,831 A | 3/1994 | Bosley | |
| 5,327,891 A | 7/1994 | Rammler | |
| 5,417,223 A * | 5/1995 | Aarnio | A61F 6/144 128/833 |
| 5,759,154 A | 6/1998 | Hoyns | |
| 6,306,125 B1 | 10/2001 | Parker et al. | |
| 6,742,520 B1 * | 6/2004 | Wildemeersch | A61F 6/144 128/830 |
| 7,252,839 B2 | 8/2007 | Hallinen et al. | |
| 2006/0016451 A1 * | 1/2006 | Hallinen | A61F 6/14 128/830 |

FOREIGN PATENT DOCUMENTS

| | | | |
|---|---|---|---|
| DE | 3209290 A1 | 12/1982 | |
| EP | 0147274 A1 | 3/1985 | |
| EP | 1400258 A1 | 3/2004 | |
| WO | 09009158 A1 | 8/1990 | |
| WO | WO 9009158 A1 * | 8/1990 | A61F 6/144 |
| WO | 0180788 A2 | 11/2001 | |

OTHER PUBLICATIONS

English Language Translation of DE2207939.
EPO English Language machine translation of DE3209290.
Written Opinion for International Patent Application No. PCT/FI2006/050123, dated Jul. 10, 2006, 7 pages.
International Search Report for International Patent Application No. PCT/FI2006/050123, dated Jul. 10, 2006, 6 pages.
International Preliminary Report on Patentability for International Patent Application No. PCT/FI2006/050123, dated Oct. 9, 2007, 8 pages.

* cited by examiner

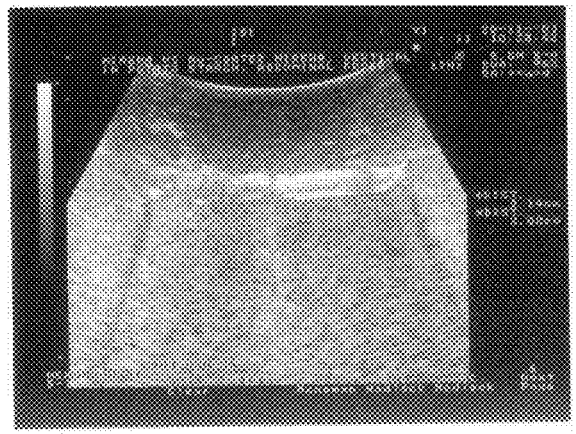
Fig. 3
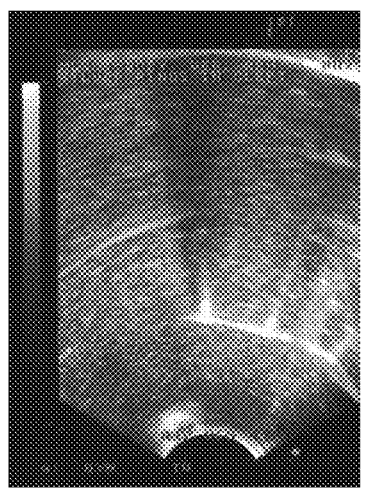 
Fig. 4_A    Fig. 4B

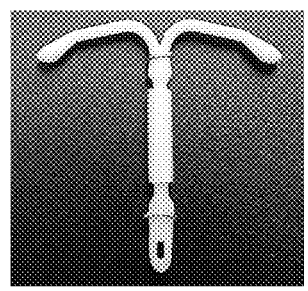
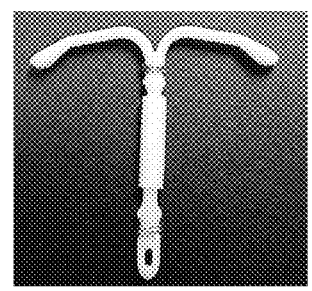
Fig. 7A          Fig. 7B
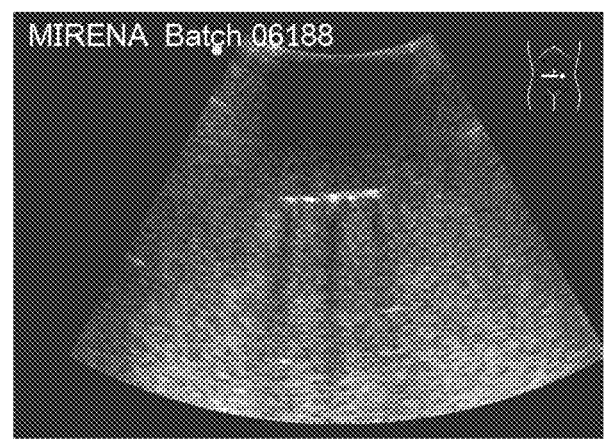
Fig. 8

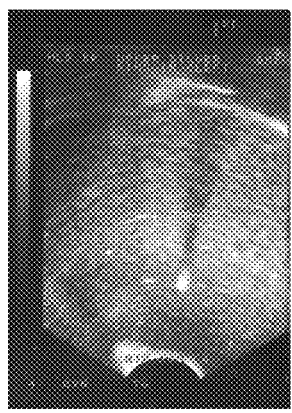 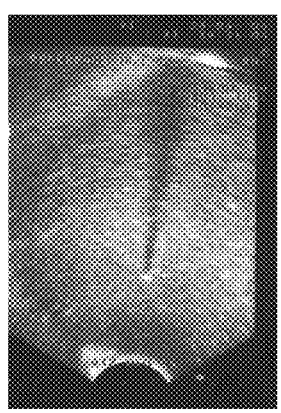 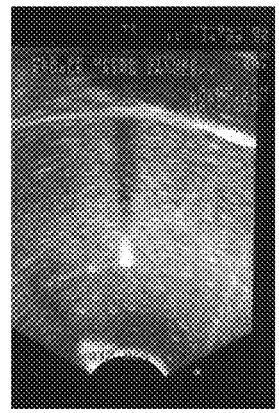
Fig. 11A  Fig. 11B  Fig. 11C
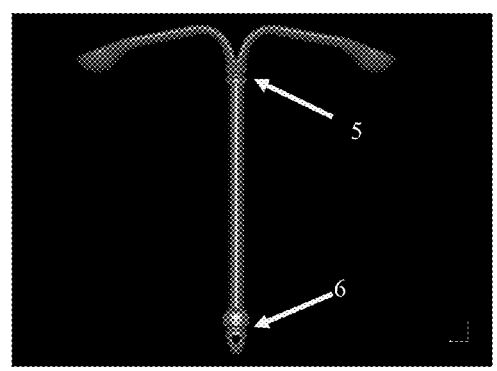
Fig. 12

ULTRASONICALLY DETECTABLE INTRAUTERINE SYSTEM AND A METHOD FOR ENHANCING ULTRASOUND DETECTION

FIELD OF THE INVENTION

The present invention relates to ultrasonically detectable intrauterine systems and to a method for enhancing ultrasound detection of these systems.

BACKGROUND OF THE INVENTION

The intrauterine systems, commonly known as IUS's, have long been known and they have been constructed in numerous shapes and sizes and of various materials. The IUS's consist normally of a plastic frame having the shape of the letter T or 7, although the shapes of letters S and ω are also possible. The IUS's which contain drugs can be used to administer these drugs locally to the uterus at a controlled release rate over a prolonged period of time. The medicated IUS's which have found considerable acceptance in contraception and hormonal treatment can be divided into copper and hormonal devices. In a copper IUD (Intra Uterine Device), a copper wire or silver cored copper wire is wound around the vertical stem of the frame whereas in a hormonal IUS a hormone containing elastomeric capsule is placed on the vertical stem. The capsule may be coated by an elastomer or polymer membrane which controls drug release from the elastomer-hormone capsule. Monofilament removal threads, used for IUS removal after the period of use, are tied to the loop at the end of the vertical stem.

Undesirable complications that have been associated with the use of IUS's are infection, bleeding, uterine perforation, cervical laceration, septic abortion, ectopic pregnancy, and expulsion of the IUS. Expulsion is undesirable, because the IUS can no longer provide protection against pregnancy. Perhaps the most common side effect of copper IUD's is abnormal bleeding, taking the form of menorrhagia, metrorrhagia, or both. This side effect is not found with hormonal IUS's, which can be actually used for the treatment of menorrhagia. A disparity between the size and/or shape of the uterine cavity and the IUS and inaccurate (non-fundal) placement of the system at the time of insertion have both been linked to IUS-induced increases in uterine bleeding.

In addition to the optimal design and composition, it is important that the IUS is placed in a proper position. For many complications, the examining physician must be able to detect the positioning and placement of the IUS in order to diagnose the problem, and to prevent further complications.

Currently, there are several techniques for determining the presence and position of IUS's in the uterus. One technique involves the use of X-rays. However, the use of X-rays in the area of uterus and ovaries should be avoided whenever possible. Another detection technique involves the use of sounds. Physicians also will often examine the marker strings, which are attached to the IUS to detect the presence and position of the IUS and at the end of usage time to remove the system. Another technique is to manipulate the uterus under fluoroscopic examination. In some cases, a second IUS has been inserted into the uterus to serve as an intra-uterine marker to detect relative placement of the lost IUS.

Ultrasound imaging is widely used in medical applications to non-invasively observe the structures within the human body. In addition to imaging physiological structures and tissue, ultrasound imaging has also been employed to image medical devices that are inserted into tissue or passageways of the patient.

The uterus is visible to ultrasound by reconciling the position of the IUS with the position of the uterus. In reconciling the relative positions of the uterus and IUS, the examining health care personnel can determine whether the IUS is properly placed within the uterus. The medical personnel will be able to determine whether the IUS has perforated the uterus or cervix. If the IUS has partially or fully perforated the uterus or cervix, the physician, by knowing the position of the IUS is better able to plan an appropriate strategy for removal of the IUS.

In a typical imaging system, short bursts of ultrasound energy are directed into a patient's body with a transducer. The returning reflected ultrasound energy, or echoes, are received by the same transducer and are converted to electrical signals. The signals representing the reflected energy are processed and formatted into a video image of a target region. The technology is especially valuable for medical imaging applications because diagnostic ultrasound procedures are safe, very acceptable to patients and less expensive than other digital imaging technologies. Also, instruments are widely available and images are produced in real time.

Most medical devices have acoustic impedance similar to that of the tissue into which the device is inserted. Consequently, visibility of the device is poor and accurate placement becomes extremely difficult if not impossible. Another problem affecting the visibility of devices is the scattering angle. For example, stainless steel needles have acoustic impedance significantly different from tissue and are highly visible under ultrasound imaging when the needle is in the plane of the ultrasound beam. If the needle is moved to some other angle off-axis, the ultrasound beam is scattered in a direction other than the transducer and the needle becomes less visible or even invisible under ultrasound imaging.

Both of the problems described above have been addressed by efforts to increase the scattering power of the device so that the device becomes visible even when it is not completely in the plane of the ultrasound beam. Various approaches have also been used to enhance ultrasonic imaging by modifying the reflective surface characteristics of these devices. A variety of ultrasound contrast agents are known, including porous uniformly sized non-aggregated particles. Contrast agents may enhance the visibility of target tissue into which they are injected, but they can not enhance the ultrasound visibility of insertable medical devices.

U.S. Pat. No. 5,201,314 describes a medical device that is insertable into tissue or a passageway and imageable with sonic imaging equipment. The device includes an elongated insertable member that has an interface having a shape that is responsive to the sonic beam for producing the image. The elongated member includes a substance such as spherically or other geometrically-shaped particles that have a predetermined contour for establishing the interface. This contoured substance is contained within the material of the elongated member or alternatively or in combination attached to or embedded in the outside surface of the member material. In one embodiment, the interface layer may include a high density metal such as titanium, tungsten, barium, bismuth, platinum, silver, gold, or palladium.

U.S. Pat. No. 6,306,125 relates to a system for delivering an implant to tissue to be treated. To enhance the visibility of the implant to imaging systems, echogenic contrast agent can be added to the implant. Alternatively an implant can contain elements, molecules, compounds or compositions, which have atomic weights sufficient to confer radiopacity to the implant. Particularly preferred radiopaque materials are, e.g. barium, gold, platinum, tantalum, bismuth and iodine. The radiopacifying agents can be incorporated into the implants in several ways. Biocompatible non-immunogenic metals such as gold and platinum may be incorporated as a very fine dispersion with particle sizes less than a few micrometers. Other heavy atoms may be incorporated in the form of inorganic salts, such as barium sulphate.

Several efforts have been made to enhance the echogenicity of medical device by modifying the surface of the device. U.S. Pat. No. 4,869,259 relates to the enhanced echogenicity of the needle by particle blasting with 50-micron particles to produce a uniformly roughened surface. U.S. Pat. No. 4,977,897 relates to sounding apertures machined into needles to match the incident beam wavelength this improving sonographic visibility. U.S. Pat. No. 5,289,831 relates to the modification of the catheters and other devices by incorporating glass spheres or high-density metal particles in the range of 0.5 to 100 microns or partially spherical indentations. U.S. Pat. No. 5,327,891 relates to the use of microbubbles containing medium contained in vanes and/or tracks to echogenically enhance catheters. U.S. Pat. No. 5,759,154 relates to the utilization of a masking technique to produce depressions comprising alternating rows of squares and diamonds on the surface around the circumference of the device.

In our studies the known internal modifications of IUS's (compounding with hollow glass microspheres, channelling, inserting a metal core in the body of an intrauterine system) did not lead to the desired effect, i.e. they did not sufficiently improve visibility of the IUS in ultrasound detection. See FIG. 1, where the difference of metal cored T-body (FIG. 1A, left side) with surface modified T-body (FIG. 1B) is shown. Any material between the probe and ultrasound enhancing material fades out partly or totally the bright echogenicity of the ultrasound visibility enhancer. However, a suitable means for improving the visibility of IUS's was found by modifying the surface of the IUS with inert metals. Although it is known that metals in general improve echogenicity in ultrasound detection, in the prior art methods metals have been used due to their contraceptive effect or to enhance detection using X-rays. This invention concentrates on means to improve ultrasound detection and to make certain parts of the T-body of the product more visible than other parts, i.e. IUS location and position in uterus can be quickly studied at the very same clinician's appointment.

SUMMARY OF THE INVENTION

The present invention thus provides an improved ultrasonically detectable intrauterine system (IUS) for relatively long-term insertion into a uterine cavity. The IUS according to the invention comprises at least one image enhancing means for the ultrasound imaging of the system. Said means are selected from the group consisting of
  a) an inert metal coating on at least part of the body of the intrauterine system;
  b) at least one inert metal clip, pin, ring and/or sleeve fixedly positioned on the body of the intrauterine system; and
  c) a metallic loop anchored to the vertical arm of the body of the intrauterine system in place of the usual loop.

The invention is also directed to a method for improving the visualization of an intrauterine system within the uterine cavity in an ultrasound examination. The method comprises i.a. the step of providing the body of an IUS with at least one inert metal clip, pin, ring and/or sleeve, applying an inert metal coating on at least part of the body of an IUS, or anchoring a metallic loop to the vertical arm of the body of an IUS. In some embodiments, the metal ring forms a closed loop and surrounds an upper end of a vertical arm of the intrauterine system. In some embodiments, the metal ring is a double ring that surrounds the upper end of a vertical arm of the intrauterine system. In some embodiments, the metal ring is at least partially embedded in an upper end of a vertical arm of the intrauterine system.

The improvement of visibility of an IUS in an ultrasound examination has the advantage of enabling health care personnel to detect more easily the positioning of the device, thereby facilitating the detection of both problems in placement of the device and problems with the device itself.

Another advantage of this feature is that the positioning of the IUS can be ascertained without a physical intrusion into the area of the body wherein the device is inserted. Transvaginal or abdominal ultrasound is nowadays a routine outpatient office procedure, which has almost completely displaced the use of X-ray examination in the detection of IUS's, in the ascertainment of the correct location of the device. The ability to detect the IUS with ultrasound examination is of vital importance in various clinical situations, such as bleeding problems, pain, suspected expulsion (i.e. displacement of the IUS), or other possible adverse effects during IUS use. The correct location is determined by ultrasound examination by measuring the distance between the upper end of the vertical stem of the system to the outer surface of the fundus of the uterus. As the uterus is not distinguishable in X-ray examination, the use of ultrasound enables the ascertainment of the correct location of the IUS more accurately than an X-ray examination, e.g. in case of a partial expulsion of the device. Further, the use of X-rays should be strictly avoided in the general user population of IUS's, i.e. fertile aged women, to minimize the exposure of reproductive organs to X-rays. Especially the ovaries are very sensitive to the potential mutagenic effects of X-rays, whereas ultrasound examination does not carry any of such inherent risks. In summary, the present invention enables the use of a safer and more reliable detection technique.

Normally 2-dimensional view is used in medical sector. Thus only horizontal arms (transverse view) or a vertical arm (sagital view) can be seen at a time with a convex probe (FIG. 2 A). By a vaginal probe sometimes also a vertical arm can be seen (FIG. 2 B).

Figure 1A:
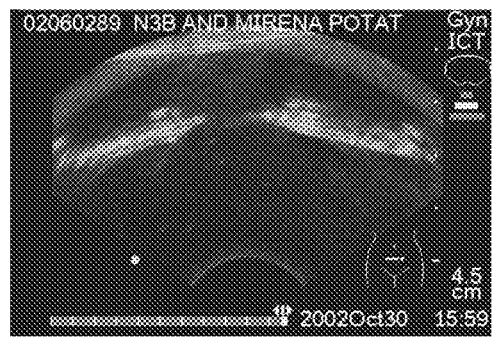
FIG. 1A Ultrasound image of a metal cored T-body on the left and reference IUS on the right.
Figure 1B:
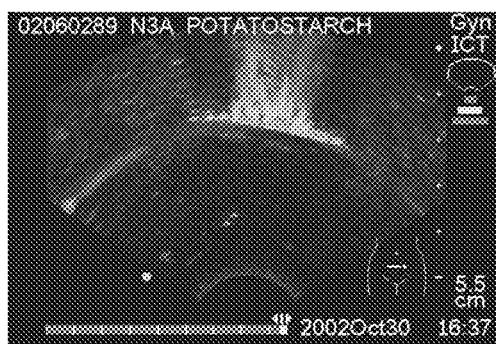
FIG. 1B Ultrasound image of a surface modified T-body (with metal). Surface modification enhanced echogenicity of T-body remarkably. The images in FIGS. 2A and 2B were taken in in vitro medium with convex probe.
Figure 2A:
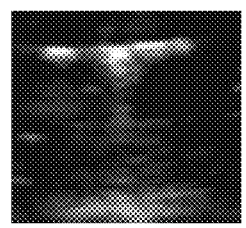

FIG. 2A. Ultrasound image of T-body, transverse view with convex-probe in water.

Figure 2B:
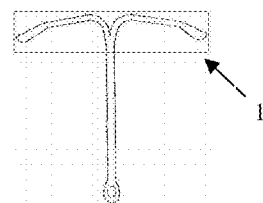

FIG. 2B A schematic model of a T-body with rectangle (1) indicating which part of T-body can be seen in the picture in FIG. 2A.

Figure 2C:
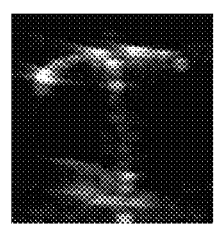

FIG. 2C Ultrasound image of a T-body, viewed from the bottom of the T-body in water with vaginal probe (also vertical arm is visible).

FIG. 3 shows a comparative sagital view of the vertical arm of a regular hormonal IUS (on the left) and a hormonal IUS with metal (Au) coated T-body (on the right). Convex probe in potato starch thickening. It is known that especially the hormone capsule of an IUS fades out the echogenicity of the material underneath it. Au-coating improved the echogenicity of the T-body and the T-body is seen as bright image inside the hormone capsule.

FIG. 4A is a comparative sagital view of the vertical arm of a T-body with metal (Ag) rings in upper and lower part of the stem compared to FIG. 4B with a regular T-body. Metal rings are seen as a bright echo behind the vertical arm. Vaginal probe in potato starch thickening.

Figure 5:
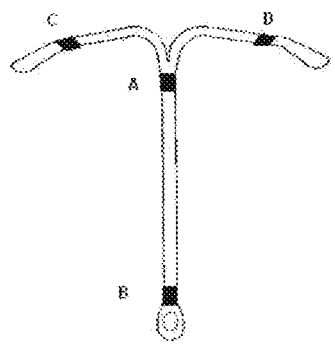

FIG. 5. A drawing of a T-body with blue bands showing optimal positions of echogenic enhancers, A, B, C, and D: Echogenicity of place A or places A-B are the most important in order to locate the distance of IUS from fundus. In order to properly outline the position of horizontal arms in uterus, echogenicity of positions C-D is important.

Figure 6:
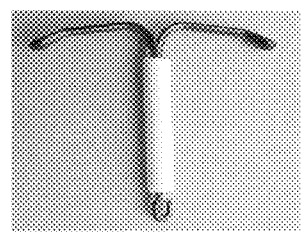

FIG. 6. A photograph of a hormonal contraceptive with Au-coated T-body.

FIG. 7A. A photograph showing unembedded Ag-rings at the upper and lower end of vertical arm of a hormonal IUS.

FIG. 7B A photograph showing embedded double-rings at the upper and lower end of the vertical arm of a hormonal IUS.

FIG. 8. An ultrasound image showing acoustic shadowing behind the horizontal arms of MIRENA®. Note triple shadowing from the thickest parts of horizontal arms. MIRENA® is a levonorgestrel-releasing intrauterine system (IUS), which consists of a hormone-elastomer capsule, mounted on a T-body and covered with an opaque tubing, which regulates the release of levonorgestrel.

Figure 9:
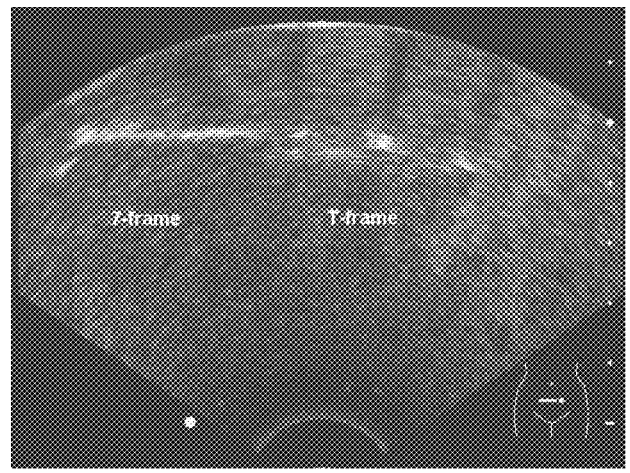

FIG. 9. Comparison of ultrasound image produced from a glass microsphere modified 7-frame to a standard T-frame in corn starch thickening by vaginal probe. The whole horizontal arm of the 7-frame is visible whereas only the three thickest parts of the T-frame and their acoustic shadowing can be seen.

Figure 10:
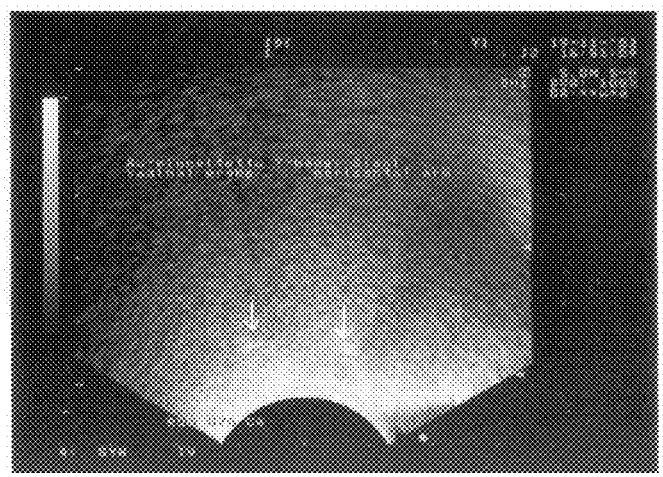

FIG. 10. Spherical ends of Au-coated T-body (marked with arrows) were located from a sponge-water system.

FIG. 11. Ultrasound pictures comparing the brightness of Ag-rings on the vertical arm (transverse view, vaginal probe) from T-bodies with: Embedded single ring (FIG. 11A), Reference (no ring) (FIG. 11B) and Embedded double ring (FIG. 11C).

FIG. 12. T-body design with positions (5 and 6) for embedded metal rings at the ends of a vertical arm.

Figure 13:
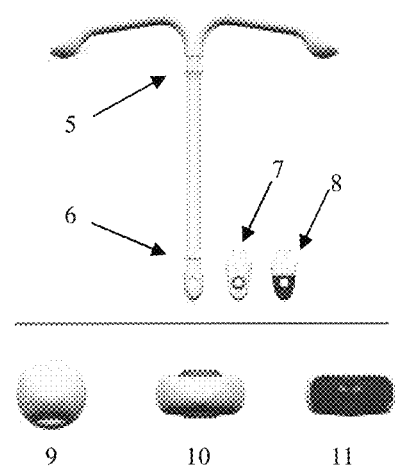

FIG. 13. A schematic picture of different loop designs (9, 10, and 11) together with T-body design for metals clips (7 and 8) at positions (5 and 6) at the ends of a vertical arm.

DETAILED DESCRIPTION OF THE INVENTION

Ultrasound visibility or echogenicity of an intrauterine device depends on the density difference of the adjacent materials, the propagation speed difference of sound in the adjacent materials, surface roughness, and the echogenicity of surrounding materials. The ultrasound visibility of different material modifications of IUS's can be estimated by evaluating the echogenicity of the material from the calculated reflected energies.

Sound travels through materials under the influence of sound pressure. Because molecules or atoms are bound elastically to one another, the excess pressure results in a wave propagating through the solid. Acoustic impedance, Z ($10^5$ g/cm$^2$ s), determines the acoustic transmission and reflection at the boundary of adjacent materials:

$$Z = \rho \cdot V$$

wherein $\rho$=density (g/cm$^3$) and V=propagation speed (mm/µs).

Reflected energy R, can be calculated from the acoustic impedances of adjacent materials ($Z_1$ and $Z_2$):

$$R = \left(\frac{Z_2 - Z_1}{Z_2 + Z_1}\right)^2$$

For transmitted sound energy: T=1−R. With these formulas the ultrasound visibility of different modifications of IUS can be estimated. The higher the reflected energy, the better the echogenicity of the material.

In Table 1, the reflected and transmitted energies of various material combinations are compared.

TABLE 1

Comparison of different material combinations

| Material 1 - Material 2 | Reflected sound energy, R | Transmitted sound energy, T |
|---|---|---|
| Human tissue - Copper | 0.860 | 0.140 |
| Human tissue - MED 4735 tubing | 0.032 | 0.996 |
| Human tissue - PDMS 373 TW tubing | 0.020 | 0.980 |
| Human tissue - PE-LD | 0.004 | 0.997 |
| Human tissue - Glass (soda lime) | 0.625 | 0.375 |

(PDMS = polydimethyl siloxane)
(PE-LD = low density polyethylene)

From Table 1 it can be seen that the copper wire of copper IUDs and glass reflect most of the sound energy back, thus providing good echogenicity and bright picture. Echogenicity of elastomers and the usual body raw material of an IUS (PE-LD and 20-24% of BaSO$_4$) is worse. Most of the sound energy is transmitted through the material.

An intrauterine system according to the invention comprises at least one image enhancing means for improving the ultrasound imaging of the system. The means are selected from the group consisting of
 a) an inert metal coating on at least part of the body of the intrauterine system,
 b) at least one inert metal clip, pin, ring and/or sleeve fixedly positioned on the body of the intrauterine system, and
 c) an inert metallic loop anchored to the vertical arm of the body of the intrauterine system in place of the usual loop.

The metal is advantageously selected so that the reflected energy at the boundary of adjacent materials is as high as possible. Preferably the metal is selected from the group consisting of inert metals, such as silver, gold, titanium, tungsten, barium, bismuth, platinum and palladium. Preferred metals are silver, gold, titanium and platinum, which are known to be compatible (i.e. physically inert) with the human body. However, copper may also be used.

In a preferred embodiment according to the invention, the metal coating or the metal clips, pins, rings or sleeves are located at the ends of the vertical arm(s) of the IUS having the shape of the letter T or 7. This enables a physician to reliably measure the distance of IUS from fundus. It is also possible to coat the "loop" at the end of the vertical arm of the IUS, or to fix a metal ring, pin or sleeve at the foot of the loop. In a further preferred embodiment, the metal coating or the metal clip, pin, ring or sleeve is located only at the "upper" end of the vertical arm of the IUS.

Sometimes it is also important to locate the position of horizontal arms of a T-body. This can be achieved by metal coating the whole T-body or by incorporating metal clips, rings or sleeves also to the end of horizontal arm(s) (before spherical ends) (FIG. 5).

Typically the thickness of the metal coating may vary from between about 0.1 nm and about 500 nm, preferably between about 1 nm and about 50 nm. However, even thicker coatings of about 0.1 mm are possible.

The metal clips, pins, rings or sleeves may be unembedded or at least partly embedded in the body of an IUS. Partial embedding of the rings smooths the surface of the IUS while not yet impairing the visibility compared to unembedded counterpart. In case of rings it is advantageous to use double rings to enhance echogenicity. In case of clips and sleeves, the broader the clip or sleeve, the better is the visibility. The width of the metal clip, pin, ring or sleeve may vary for example from 0.2 to few millimetres, being preferably about 1 mm, or in case of double rings about 0.5 mm A further embodiment is to fix a metal pin of an appropriate size through the loop, so that the ends of the pin which are larger than the diameter of the loop are visible.

The intrauterine system according to the invention may also have locking means, typically at least two locking parts, between which the medicated capsule is mounted. The locking parts keep the capsule in the correct position during the insertion, use and removal of the IUS. Said locking parts may have different shapes, e.g. a shape of a truncated cone. They can be made of a polymeric material, which can be the same or different from the material of the body, but other materials can also be used, for example in this case an inert metal which improves visibility of the IUS in an ultrasound examination.

The intrauterine system according to the invention has been designed for a relatively long-term insertion into a uterine cavity. However, a long-term insertion may vary greatly, for example from a couple of weeks to several years, the maximum IUS usage time being typically up to five years.

The invention is also directed to a method for improving the visualization of an intrauterine system within the uterine cavity in an ultrasound examination, comprising at least one of the steps of
- applying an inert metal coating on at least part of the body of an IUS, or
- providing the body of an IUS with at least one inert metal clip, pin, ring and/or sleeve, or
- anchoring a metallic loop to the vertical arm of the body of an IUS;

inserting the IUS into the uterine cavity and examining the position of the IUS within the uterine cavity in an ultrasound examination at an appropriate point of time.

EXPERIMENTAL

Experimental in vitro Conditions:
  PE-container filled with water, corn starch thickening or potato starch thickening
  Test specimen placed inside a sponge and the system immersed into water
Apparatus:
  Sonosite 180PLUS, with convex (2-4 MHz) and vaginal (4-7 MHz) probes or
  Aloka SSD 900, with convex (3.5 MHz) and vaginal (7.5 MHz) probes Studied Modifications:
  Group 1: Hollow glass microspheres have been incorporated in the raw material of the frames (bodies). Due to high density and entrapped air inside, the echogenicity should be improved.
  Group 2: Hollow glass microspheres have been incorporated in the hormone-releasing core.
  Group 3: The whole T-body is Au-coated using Jeol Fine Coat ion sputter JFC-1100 equipment (1 kV voltage and 1 mA current for 20 minutes). The obtained thickness of the Au-layer was few nanometers. See FIG. 6.
  Group 4: Rings or double rings of 0.5 mm thick silver wire were positioned adjacent to the ends of the vertical arm of the T-body. Both embedded and unembedded fixing was investigated with the currently available T-frames. A rough embedding was made manually by scooping out a channel with depth of about 0.25 mm. See FIG. 7.
Other in vitro Conditions:
  Potato starch and corn starch thickenings behaved similarly in the sonography.
  The scattering and attenuation of sound waves and the avoidable presence of air in the sponge system was so high that only NOVA T® 380 (vertical arm) was located. (NOVA T® is a T-shaped plastic frame, which has a copper wire or a silver cored copper wire surrounding the vertical arm of the T.)
  Water as an in vitro medium was found worse than the other media due to too good echogenicity of studied specimens in water. No differences in echogenicity between the samples were detected. Sound wave proceeds easily through water and no disturbing echoes are formed. Acoustic shadowing, the typical phenomenon of IUD's and IUS's is very difficult to be detected in water as water is seen black in a sonograph. (In FIG. 8 an example of the acoustic shadowing of MIRENA® in potato starch thickening is presented.)
Comparison of Different Modifications:
  Glass microspheres in T-frame improved echogenicity slightly. See FIG. 9 where glass microsphere modified 7-frame and standard T-frame are compared in corn starch thickening.
  Au-coating improved echogenicity of T-body. T-body is seen as a bright image under hormone releasing capsule. See FIG. 3. Even in the sponge system which was found to be very challenging in vitro medium, the spherical ends were located. See FIG. 10.
  0.5 mm thick Ag-wire placed on the upper and lower ends of the vertical arm enhanced the echogenicity. See FIG. 4. Metal rings were seen as bright white spots and their location during investigation was easy. Partial embedding of the rings did not impair the visibility compared to unembedded counterpart in any projections. However, it was obvious that a double ring behaved better than a single ring. The sonograph from double rings was larger and brighter. See a comparative picture, FIG. 11, where the ring, double-ring and no-ring have been examined in optimal projection.

The invention claimed is:

1. An ultrasonically detectable intrauterine system (IUS) for long-term insertion into a uterine cavity comprising:
  a vertical arm having an upper end and a lower end;
  horizontal arms extending from the upper end of the vertical arm;
  a hormone-containing capsule mounted on the vertical arm; and an image enhancing structure adapted to improve ultrasound imaging of the IUS, wherein the image enhancing structure comprises an inert metal ring, wherein:
the inert metal ring is composed of silver and has a width of 0.2 mm to 1 mm;
the inert metal ring surrounds the upper end of the vertical arm and is at least partially embedded in the upper end of the vertical arm; and
the inert metal ring does not comprise an active ingredient.

2. The IUS of claim 1, further comprising at least two locking structures to keep the hormone-containing capsule in correct position during insertion, use and removal of the IUS.

3. The IUS of claim 1 wherein:
the hormone-containing capsule is a hormone-elastomer capsule that regulates a release of levonorgestrel and
the inert metal ring comprises a double ring that surrounds the upper end of the vertical arm.

4. The IUS of claim 1, wherein the inert metal ring comprises 0.5 mm thick wire.

5. The IUS of claim 1, wherein the inert metal ring is disposed within a 0.25 mm deep channel formed in the upper end of the vertical arm.

6. A method to form an intrauterine system (IUS) with improved visibility within a uterine cavity in an ultrasound examination, the method comprising:
forming a vertical arm of the IUS with a medicated capsule mounted thereto;
forming a first portion of one of an upper end of the vertical arm, a lower end of the vertical arm, and an end of a horizontal arm extending from the upper end of the vertical arm; and
surrounding the upper end of the vertical arm with an inert metal ring, wherein the inert metal ring is composed of silver, does not comprise an active ingredient, has a width of 0.2 to 1 mm, and is at least partially embedded in the upper end of the vertical arm.

7. The method of claim 6, further comprising forming at least two locking structures on the vertical arm to keep the medicated capsule in correct position during insertion, use and removal of the IUS.

8. The method of claim 6, further comprising:
forming a channel in the upper end of the vertical arm, wherein the channel is 0.25 mm; and disposing the inert metal ring within the channel to partially embed the inert metal ring within the upper end of the vertical arm.

9. The method of claim 6, further comprising:
surrounding the lower end of the vertical arm or the end of the horizontal arm with a second inert metal ring, wherein the second inert metal ring is composed of silver.

10. The method of claim 6, wherein the medicated capsule is a hormone-elastomer capsule that regulates a release of levonorgestrel.

11. The IUS of claim 1 wherein the hormone-containing capsule is a hormone-elastomer capsule that regulates a release of levonorgestrel.

12. A method for improving the visualization of an intrauterine system within the uterine cavity in an ultrasound examination comprising
providing an IUS according to claim 1, and
inserting the IUS into the uterine cavity and examining the position of the IUS within the uterine cavity in an ultrasound examination.

13. The IUS of claim 1, wherein the inert metal ring is composed of a silver wire.

14. The IUS of claim 1 comprising only one inert metal ring.

15. The method of claim 6 comprising only one inert metal ring.

16. The IUS of claim 1, wherein the IUS is a hormonal device only, wherein the hormone-containing capsule comprises the only active hormonal ingredient.

17. The method of claim 6, wherein the IUS is a hormonal device only, wherein the hormone-containing capsule comprises the only active hormonal ingredient.

* * * * *